United States Patent [19]
Marples et al.

[11] Patent Number: 5,304,551
[45] Date of Patent: Apr. 19, 1994

[54] ANTI-FUNGAL COMPOUNDS

[75] Inventors: Brian A. Marples; Reginald J. Stretton, both of Loughborough, England

[73] Assignee: British Technology Group Limited, London, England

[21] Appl. No.: 941,098

[22] PCT Filed: May 3, 1991

[86] PCT No.: PCT/GB91/00710
§ 371 Date: Oct. 27, 1992
§ 102(e) Date: Oct. 27, 1992

[87] PCT Pub. No.: WO91/16898
PCT Pub. Date: Nov. 14, 1991

[30] Foreign Application Priority Data
May 4, 1990 [GB] United Kingdom ............... 9010087

[51] Int. Cl.$^5$ ............................................. A61K 31/56
[52] U.S. Cl. .................................... 514/182; 514/858
[58] Field of Search ................................. 514/182, 858

[56] References Cited
U.S. PATENT DOCUMENTS
4,681,876  7/1987  Marples et al. .................... 514/182

FOREIGN PATENT DOCUMENTS
0168229  1/1986  European Pat. Off. .

OTHER PUBLICATIONS

Chemical Abstracts 107: 198742n, 1987.
Chemical Abstracts 107: 198739s, 1987.
Chemical Abstracts 107: 7433e, 1987.
Stoll et al., "Some Physical Factors Affecting the Enhanced Blepharoptotic Activity . . . ", Journal of Pharmaceutical Sciences, 1969, 58(12), pp. 1457-1459.
Goodman Gilman et al. (Editors), *The Pharmacological Basis of Therapeutics* (6th Ed.), MacMillan Publishing Company, New York, 1980, p. 1238 especially.
X. Zhu et al., "Allomerization of cholic acid and conversion to petromyzonol", Can. J. Chem. 65, 2447-2449 (1987).
A. A. Malik et al., "Selective reduction of the fomylated bile acids to the corresponding formylated bile alcohols analogs", Organic Preparations and Procedures Int. 19, 1-7 (1987).
A. A. Malik et al., "Selective protection of the side chain hydroxy group in bile alcohol derivatives", Organic Preparations and procedures Int. 18, 345-352 (1986).
"Selective Toxicity" by Adrian Albert, 7th Edition, Chapman & Hall 1985, 603-606.
Marshall et al "Aspects of the effect of bile . . . " Journal of Medical and Veterinary Mycology, vol. 25, No. 5, 1987, pp. 307-318.
Bellini et al "Derivati dell'acido litocolico . . . " Farmaco, Ed. Sci. vol. 39, No. 4, Apr. 1984, pp. 305-315.

*Primary Examiner*—Frederick E. Waddell
*Assistant Examiner*—Minna Moezie
*Attorney, Agent, or Firm*—Nixon & Vanderhye

[57] ABSTRACT

Compounds of the general formula (7):

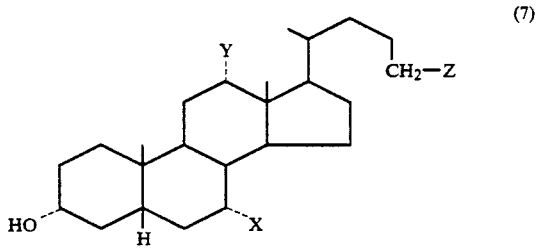

wherein X is a hydrogen atom or a hydroxyl group, Y is a hydrogen atom or a hydroxyl group and at least one of X and Y is a hydroxyl group and Z is a hydroxyl group or a methylol (—CH$_2$OH) group, have anti-fungal activity, especially against organisms selected from Candida spp. and the athlete's foot/ringworm organisms *Trichophyton mentagrophytes* and *Microsporum audonii*. Compounds in which Z is a methylol (—CH$_2$OH) group are claimed per se.

5 Claims, No Drawings

ANTI-FUNGAL COMPOUNDS

BACKGROUND OF THE INVENTION

1. Field of the Invention

The invention relates to the anti-fungal use of certain steroids.

2. Description of the Prior Art

UK Patent 2161380 B (National Research Development Corporation) describes the anti-fungal, especially anti-candida use of, bile acids and derivatives thereof, collectively having the formula

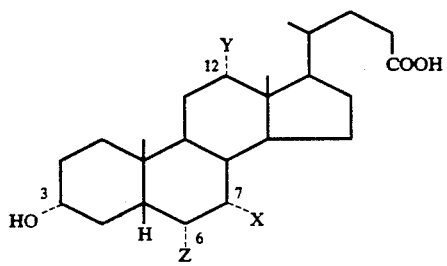

(1)

wherein each of X, Y and Z independently represents a hydrogen atom or a hydroxyl group or a derivative thereof which is a conjugate formed between the carboxyl group and the $NH_2$ group of an amino acid, and their pharmaceutically acceptable salts.

It has been a problem to find alternative anti-fungal compounds having improved therapeutic action against various fungi invasive to the human body.

SUMMARY OF THE INVENTION

It has now been found that compounds of the general formula (7):

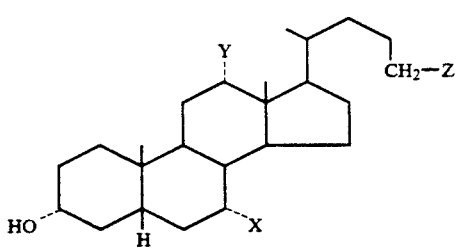

(7)

wherein X is a hydrogen atom or a hydroxyl group, Y is a hydrogen atom or a hydroxyl group and at least one of X and Y is a hydroxyl group and Z is a hydroxyl group or a methylol (—$CH_2OH$) group, have useful anti-fungal activity. Against some fungi, at least, activity appears to be better than is obtainable from the bile salts of the prior patent. Such fungi include Candida species and the fungi implicated in athlete's foot and ringworm (*Trichophyton mentagrophytes* and *Microsporum audonii*). The compounds of the invention are of particular interest for topical application.

The compounds of general formula (7) wherein Z is a hydroxyl group are known compounds. Insofar as such compounds might have no previously described medical use, this invention comprises the first medical use thereof and insofar as they might have a previously described medical use, this invention comprises the specific second medical use thereof as anti-fungal agents, said uses to be claimed in the conventional manner appropriate to national patent law. Thus, in particular, the invention, in EPC countries, includes the use of a compound of formula (7) for the manufacture of a medicament for the therapeutic application of treating fungal infections, especially by topical application, while for US purposes it includes a method of treatment of a fungal infection in a human patent, which comprises administering to the patient, preferably topically, a therapeutically effective amount of a compound of formula (7).

The invention includes particularly a pharmaceutical composition, especially for topical application, comprising a compound of formula (7) in association with a pharmaceutically acceptable carrier or diluent.

Compounds of formula (7) wherein Z is a methylol group are believed to be novel compounds and are therefore claimed as such. These compounds have one additional carbon atom in their side-chain compared to the bile acids or the bile alcohols (Z=OH).

DESCRIPTION OF THE PREFERRED EMBODIMENTS

Investigations into the effectiveness of various bile acid derivatives has shown that the compounds of the invention have a greater activity against at least one of the three selected fungal strains than the corresponding bile salts of formula (1). These tests are reported below. They indicate in particular that the following compounds of formula (7) are particularly effective against the following organisms:

| | |
|---|---|
| X = OH, Y = H ("chenodeoxycholic"), Z = OH | vs *Microsporum audonii* and *Trichophyton mentagrophytes* |
| X = H, Y = OH ("deoxycholic"), Z = OH or —$CH_2OH$ | vs. *Microsporum audonii* and *Trichophyton mentagrophytes* |
| X = OH, Y = OH ("cholic") Z = —$CH_2OH$ | vs. *Trichophyton mentagrophytes* |

The above-recited compounds or groups of compounds are accordingly preferred.

The compounds of the invention exhibit optical isomerism through an asymmetric carbon atom at the 21-position. The invention includes the individual isomers, which can be resolved by conventional means, as well as mixtures thereof.

The compounds of the invention are particularly useful in treating candidiasis and infections by dermatophytes. (Dermatophytes are fungi which cause infections of skin, hair and nails in humans and animals). In particular they are useful against fungi of the genera Trichophyton, especially *Trichophyton mentagrophytes* and rubrum, and Microsporum. Dermatophytes have many shared antigenic components.

The anti-fungal compounds of formula (7) can be formulated in any conventional way suitable for topical application, bearing in mind that they are water-insoluble. Thus, they can be formulated, for example, as a capsule, suppository or pessary for intracavital application (to the vagina, urethra or rectum) or a gel, ointment, cream or the like, dusting powder or aerosol spray. A suppository or pessary may contain theobroma oil, glycerinated gelatin or polyethylene glycol, for example, as a carrier which melts at body temperature or dissolves in body fluids. The compound of formula (7) can be formulated as an ointment or cream with an oleaginous or waxy binder. An aqueous phase may be present, to provide a cream. Other forms of formulation include gelatin capsules containing the ingredient in a liquid diluent, mixtures with talc or the like to provide dusting powder and aerosol bombs which comprise the ingredient and an inert propellant. Pessaries can be formulated as controlled release compositions using as excipient a polymeric carrier comprising residues which are cross-linked through urethane groups and which comprise polyethylene oxide, as described in UK Patent Specification 2047093 A (National Research Development Corporation).

A preferred formulation is an ointment or cream containing say, from 1 to 5 percent by weight of the compound of formula (7) depending on its effectiveness.

For athlete's foot and ringworm formulations it could be advisable to include dodecyl sulphate in the product. On testing, this had activity against *M. audonii* and *T. mentagrophytes* and was at least additive in activity with bile salts.

A particularly preferred aspect of the invention comprises the compound of formula (7) in association with an anti-inflammatory agent, especially of the steroidal type, most especially a corticosteroid, e.g. betamethasone, fluocinolone acetonide, beclomethasone dipropionate, hydrocortisone, cortisone or cortisol. These compositions are useful for the treatment of fungal infections of the skin.

A reasonable prediction from the information available is that the invention would be particularly useful in treating the same kinds of topical fungal infections as miconazole.

It is contemplated that the compounds of formula (7) could also be formulated as an aerosol for application to the orapharynx or upper respiratory tract, orally or intranasally. In principle, they could also be administered systemically, e.g. as tablets, pills and capsules for oral ingestion.

The following tests were carried out, comparing compounds of formula (7) with their prior art counterparts of formula (1).

TESTS

Organisms

*Candida albicans* NCYC 597; *Trichophyton mentagrophytes* NCPF 224 and *Microsporum audounii* NCPF 638 were used throughout as test organisms. These are open deposits at the National Collection of Yeast Cultures, Norwich UK and the National Collection of Pathogenic Fungi of the Commonwealth Mycological Institute, Kew UK.

Media

All organisms were maintained in a nutrient broth containing (gl$^{-1}$): Lab Lemco (Oxoid), 5; Peptone (Oxoid), 5; NaCl, 10. Cultures for testing antimicrobial activity were grown in this medium for 18h prior to use.

Solidified media were prepared by the addition of Agar (Oxoid No. 3) 1.5% w/v.

Antifungal Activity

Antifungal activity was estimated using solutions of the compound (as the free acid) in dimethyl sulphoxide. A range of concentrations was used for each compound to permit calculation of an approximate MIC. 13 mm discs (Whatman) were soaked in a solution of the appropriate dilution, either allowed to dry, or placed directly onto the surface of nutrient agar plates seeded with the required test organism.

After 24h incubation the diameters of zones of inhibition were measured. After a further 24h incubation, the plates were re-examined and zones re-measured.

The results are shown in the following Table:

| Basic Skeleton of Compounds | MICs μg/ml | | |
|---|---|---|---|
| | Prior Art Formula (1) | This invention Formula (2), | |
| | | Z = OH | Z = CH$_2$OH |
| 3α-OH ("lithocholic", X = H, Y = H) | | | |
| C. albicans | 410 | | |
| T. ment. | | | |
| M. aud. | 100 | | |
| 3α, 7α-OH ("chenodeoxycholic", X = OH, Y = OH) | | | |
| C. albicans | 140 | 7000 | 110 |
| T. ment. | 1300 | 30 | NONE |
| M. aud. | 1000 | 50 | 270 |
| 3α, 12α-OH "deoxycholic", X = OH, Y = H) | | | |
| C. albicans | 2100 | 730 | 150 |
| T. ment. | 300 | 10 | 30 |
| M. aud. | 30 | 10 | 5 |
| 3α, 7α, 12α-OH ("cholic") X = OH, Y = OH | | | |
| C. albicans | 390 | 900 | 450 |
| T. ment. | 10000 | 1650 | 100 |
| M. aud. | 5500 | 3800 | 20–50 |

From the above Table it will be seen that the deoxycholane and hemodeoxycholane were outstanding against the athlete's foot and ringworm organisms and that several of the other compounds had valuable activity. Generally, those compounds exhibiting a minimum inhibitory concentration of 100 μg/ml. or less are preferred.

The following Examples illustrate the preparation of compounds of the invention. A flow sheet is provided to indicate the general route. Some of the compounds prepared have two melting parts shown. The crystals melt, solidify and re-melt, apparently the result of polymorphism.

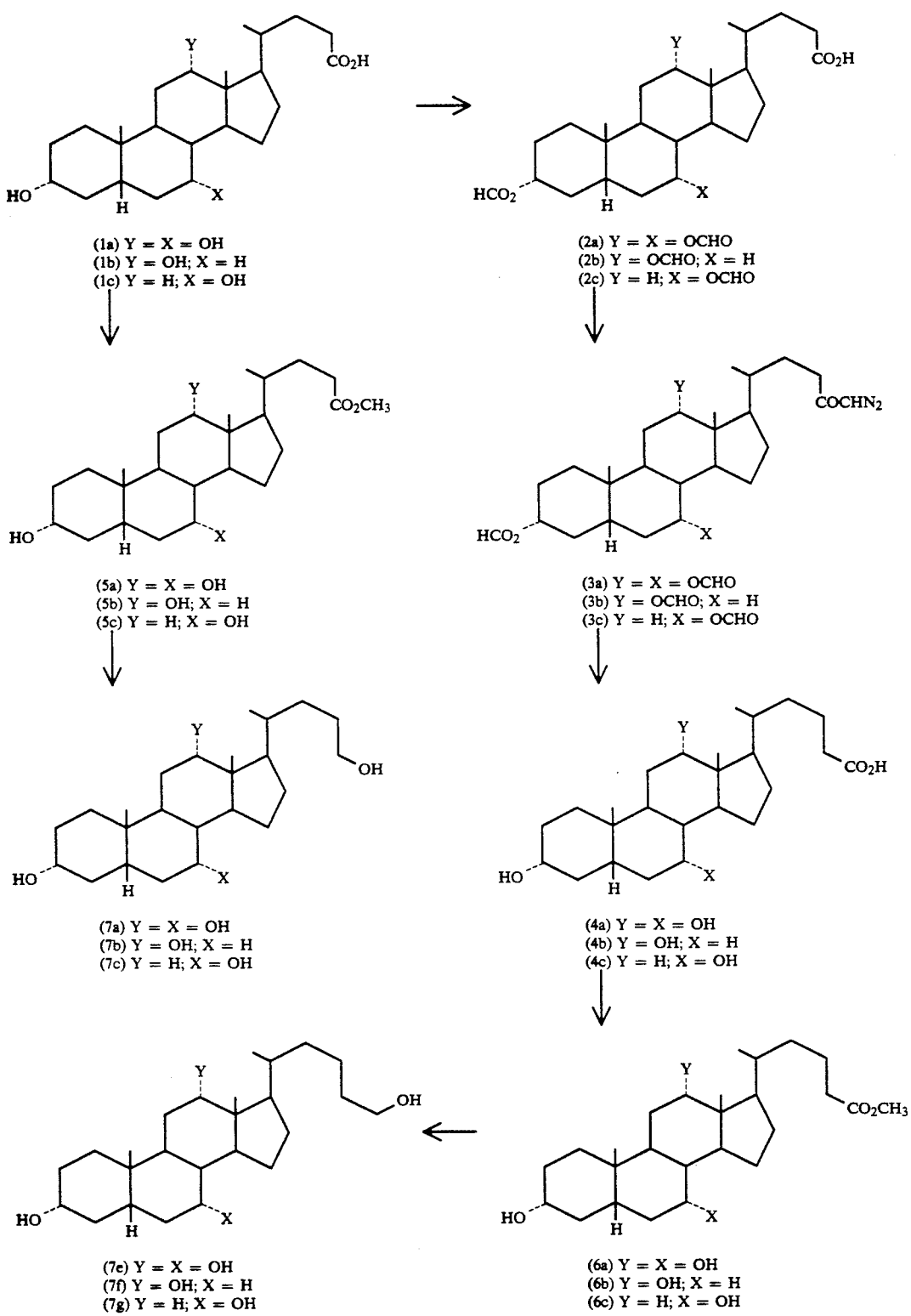

1. Preparation of 3α,7α,12α-triformoxy-5β-cholan-24-oic acid(2).

Cholic acid (15.0 g, 36.8 mmol) in formic acid was stirred at 55° C. for 4 hours and then allowed to stand at ambient temperature overnight. The resultant mixture was then evaporated to dryness. and dissolved in benzene. Further evaporation to remove any residual formic acid afforded a white solid (18.0g, 99.5%). Recrystallisation from ethanol gave 3α,7α,12α-triformoxy-5β-cholan-24-oic acid (2a)[1] (12.8 g, 71%), which appeared pure by tlc and by $^1$H nmr: (60 MHz; CDCl$_3$) δ 0.77 (3H, s, 18-CH$_3$), 0.95 (3H, s, 19-CH$_3$), 4.3–5.1 (1H, m, 3β-H), 5.0–5.2 (1H, m, 7β-H, 5.2–5.4 (1H, m, 12β-H, 8.02 (1H, s, 3-OCHO), 8.12 (1H, s, 7-OCHO), 8.17 (1H, s, 12-OCHO), 9.5–10.0 (1H, m, exchanges on adding D$_2$O, 24-OH).

2. Preparation of 3α,12α-diformoxy-5β-cholan-24-oic acid (2b).

Deoxycholic acid (15.0 g, 38.2 mmol) in formic acid was stirred at 55° C. for 4 hours and then allowed to stand at ambient temperature overnight. The resultant mixture was then evaporated to dryness and dissolved in benzene. Further evaporation to remove any residual formic acid afforded a white solid (17.1 g, 99.8%). Recrystallisation from ethanol gave 3α,12α-diformoxy-5β-cholan-24-oic acid (2b)[2] (13.9g, 81%), which appeared pure by tlc and by $^1$H nmr: (60 MHz; CDCl$_3$) δ 0.75 (3H, s, 18-CH$_3$), 0.93 (3H, s, 19-CH$_3$), 4.5–5.2 (1H, m, 3β-H), 5.2–5.4 (1H, m, 12β-H), 8.04 (1H, s, 3-OCHO), 8.15 (1H, s, 12-OCHO), 8.8–9.5 (1H, m, exchanges on adding D$_2$O, 24-OH).

3. Preparation of 3α,7α-diformoxy-5β-cholan-24-oic acid (2c)

Chenodeoxycholic acid (9.3 g, 23.7 mmol) in formic acid was stirred at 55° C. for 4 hours and then allowed to stand at ambient temperature overnight. The resultant mixture was then evaporated to dryness and dissolved in benzene. Further evaporation to remove any residual formic acid afforded a white solid. (10.5 g, 99%). Recrystallisation from ethanol gave 3α,7α-diformoxy-5β-cholan-24-oic acid (2c)[3] (8.0 g, 75%), which appeared pure by tlc and by $^1$H nmr: (60MHz; CDCl$_3$)δ0.77 (3H, s, 18-CH$_3$), 0.97 (3H, S, 19-CH$_3$), 4.3–5.0 (lH, m, 3β-H), 4.9–5.2 (1H, m, 7ft-H), 7.1–7.5 (1H, m. exchanges on adding D$_2$O, 24-CH), 8.02 (1H, s, 3-OCHO), 8.09 (lH, s, 7-OCHO).

4. Preparation of 3α,6α,12α-triformoxy-24-oxo-25-diazo-25-homo-5β-cholane (3a)

To 3α,7α-triformoxy-5β-cholan-24-oic acid (2a) (1.0 g, 2.0 mmol) was added freshly distilled thionyl chloride (2.5 ml). The reaction was allowed to proceed at room temperature for 2 hours. The excess thionyl chloride was then removed in vacuo, and the residue dissolved in benzene and re-evaporated to remove any last traces of thionyl chloride. The crude acid chloride was then dissolved in benzene (50 ml), and added dropwise to diazomethane in diethyl ether (about 1 g in 50 ml, prepared from diazald in the normal manner) at 0° C. The reaction was then allowed to stand at room temperature overnight. Evaporation gave a yellow foam which recrystallised from methanol to give a yellow solid (0.65 g, 62%). Tlc showed some trace impurities, but $^1$H nmr showed the product to be essentially pure 3α,7α,12α-triformoxy-24-oxo-25-diazo-25-homocholane (3a)[1]. 1H nmr: (60 MHz; CDCl$_3$) δ 0.77 (3H, s, 18-CH$_3$), 0.97 (3H, s, 19-CH$_3$). 4.4–5.0 (1H, m, 3β-H), 5.0–5.2 (1H, m, 7β-H), 5.25 (1H, s, 25-H), 5.2–5.4 (1H, m, 12β-H), 8.09 (1H, s, 3-OCHO), 8.18 (1H, s, 7-OCHO), 8.23 (1H, s, 12-OCHO). The product was considered to be pure enough to proceed to the following reaction to produce the homo acid.

5. Preparation of 3α,12α-diformoxy-24-oxo-25-diazo-25-homo-5β-cholane (3b)

To 3α,12α-diformoxy-5β-cholan-24-oic acid (2b) (1.0 g, 2.2 mmol) was added freshly distilled thionyl chloride (2.5 ml). The reaction was allowed to proceed at room temperature for 2 hours. The excess thionyl chloride was then removed in vacuo, and the residue dissolved in benzene and re-evaporated to remove any last traces of thionyl chloride. The crude acid chloride was then dissolved in benzene (10 ml), and added dropwise to diazomethane in diethyl ether (about 1 g in 50 ml, prepared from diazald in the normal manner) at 0° C. The reaction was then allowed to stand at room temperature overnight. Evaporation gave a yellow foam (1.1 g. 100%) which would not recrystallise. Tlc showed some trace impurities, but 1H nmr showed the product to be essentially pure 3α,12α-diformoxy-24-oxo-25-diazo-25-homocholane (3b)[2], 1H nmr: (60 MHz; CDCl$_3$) δ 0.73 (3H, s, 18-CH$_3$), 0.92 (3H, s, 19-CH$_3$), 4.5–5.1 1H, m, 3β-H), 5.18 (1H, s, 25-H), 5.1–5.4 (1H, m, 12β-H), 7.97 (1H, s, 3-OCHO), 8.07 (1H, s, 12-OCHO); IR (neat) 2100, 1716 (24-CO), 1638 (25-C-N=N) cm$^{-1}$. The product was considered to be pure enough to proceed to the following reaction to produce the homo acid.

6. Preparation of 3α,7α-diformoxy-24-oxo-25-diazo-25-omo-5β-cholane (3c)

To 3α,7α-diformoxy-5β-cholan-24-oic acid (2c) (2.1 g, 4.7 mmol) was added freshly distilled thionyl chloride (5.0 ml). The reaction was allowed to proceed at room temperature for 2 hours. The excess thionyl chloride was then removed in vacuo, and the residue was dissolved in benzene and re-evaporated to remove any last traces of thionyl chloride. The crude acid chloride was then dissolved in benzene (100 ml), and added dropwise to diazomethane in diethyl ether (about 2 g in 100 ml, prepared from diazald in the normal manner) at 0° C. The reaction was then allowed to stand at room temperature overnight. Evaporation gave a yellow oil which recrystallised from ethanol to give a yellow solid (2.0 g, 90% ). Tlc showed some trace impurities, but $^1$H nmr showed the product to be essentially pure 3α,7α-diformoxy-24-oxo-25-diazo-25-homocholane (3c)[3], 1H nmr: (60 MHz; CDCl$_3$) δ 0.65 (3H, s, 18-CH$_3$), 0.96 (3H, s, 19-CH$_3$), 4.4–5.0 (1H, m, 3β-H), 4.9–5.2 (1H, m, 7β-H), 5.23 (1H, s, 25-H), 8.04 (1H, s, 3-OCHO), 8.10 (1H, s, 7-OCHO). The product was considered to be pure enough to proceed to the following reaction to produce the homo acid.

PREPARATION OF THE HOMO ACIDS

7. Preparation of 25-homocholic acid (4a)

3α,7α,12α-triformoxy-24-oxo-25-diazo-25-homocholane (3a) (1.3 g, 2.5 mmol) in collidine (4 ml) and benzyl alcohol (4 ml) was added to a preheated flask at 200° C. and heated with stirring at 180°–200° C. for 15 minutes. The reaction mixture was then cooled to ambient temperature, diluted with water (50 ml) and extracted into diethyl ether (4×). The combined ether extracts were then washed with water (1×), 2M HCl (2×), water (1×), sat. NAHCO$_3$ solution (1×), and water (3×), dried (MgSO$_4$) and evaporated. The resultant gum was then hydrolysed by dissolving in 10% methanolic KOH (40 ml) and refluxing for 1.5 hours. The resultant mixture was cooled to 0° C. and quenched with water (20 ml) and 2.5% K$_2$CO$_3$ solution (40 ml). The basic solution was then washed with ethyl acetate (3×) to remove the benzyl alcohol, acidified with 2M HCl and extracted into diethyl ether (3×). The combined ether extracts were washed with water (3×), dried (MgSO$_4$) and evaporated to afford a cream-coloured solid (0.91 g, 86%). Recrystallisation from acetone/dichloromethane gave a white solid (0.58 g, 55%). Tlc showed a trace of impurity, but $^1$H nmr, $^{13}$C nmr and IR showed the compound to be essentially pure 25-homocholic acid (4a)[1]: m.p. 218°-220° C. (softens at 215° C.) (Lit. 219.5°-220° C.[1a], 216°-218° C.[1b]); $^1$H nmr (90 MHZ; CDCl$_3$/DMSO d$_6$) δ 0.66 (3H, s, 18-CH$_3$), 0.87 (3H, s, 19-CH$_3$), 2.1-2.3 (2H, t[broadened], 24-CH$_2$), 3.0-3.6 (1H, m, 3β-H), 3.6-3.8 (1H, m, 7β-H), 3.8-4.0 (1H, m, 12β-H); $^{13}$C nmr (pyridine d$_5$/CD$_3$CN) δ 11.5 (C-18), 16.4 (C-21), 20.9 (C-23), 21.6 (C-19), 22.3 (C-15), 25.9 (C-9, 26.8 (C-16), 27.9 (C-11), 29.9 (C-2), 33.8 (C-6, C-10), 34.2, 34.7 (C-1, C-20, C-22, C-24), 39.1 (C-4, C-8), 41.1 (C-5, C-14), 45.5 (C-13), 46.0 (C-17), 66.6 (C-7), 70.5 (C-3), 71.4 (C-12), 176.4 (C-25); IR 3490, 3350 (OH's), 1707 (C=O) cm$^{-1}$.

The product was recrystallised twice more from acetone/dichloromethane before submitting for testing. Although tlc still showed some trace impurity on charring the plate, gas chromatography on the methyl ester (6a) [see below for details of prep.] showed the compound submitted for testing to be 99% pure. [GC procedure: The methyl ester (6a) (10 mg) was dissolved in pyridine (1.0 ml) and treated with hexamethyldisilazane (0.2 ml and trimethylchlorosilane (0.1 ml); 0.2 μl of this solution was injected onto a BP-1 column 25 m×0.2 mm at 282° C.; chart speed 1.0 cm/min. Retention time 16.1 min; cf. retention time for methyl cholate=13.6 min. The BP-1 column is a bonded phase non-polar dimethylsiloxane column supplied by SGE UK Ltd.]

8. Preparation of 25-homodeoxycholic acid (4b).

3α,12α-(x-diformoxy-24-oxo-25-diazo-25-homocholane (3b) (3.0 g, 6.3 mmol) in collidine (5 ml) and benzyl alcohol (5 ml) was added to a preheated flask at 200° C. and heated with stirring at 180°-200° C. for 15 minutes. The reaction mixture was then cooled to ambient temperature, diluted with water (50 ml) and extracted into diethyl ether (4×). The combined ether extracts were then washed with water (1×), 2M HCl (2×), water (1×), sat. NaHCO$_3$ solution (1×), and water (3×), dried (MgSO$_4$) and evaporated. The resultant gum was then hydrolysed by dissolving in 10% methanolic KOH (60 ml) and refluxing for 1.5 hours. The resultant mixture was cooled to 0° C. and quenched with water (30 ml) and 2.5% K$_2$CO$_3$ solution (60 ml). The basic solution was then washed with ethyl acetate (3×) to remove the benzyl alcohol, acidified with 2M HCl and extracted into diethyl ether (3×). The combined ether extracts were washed with water (3×), dried (MgSO$_4$) and evaporated to afford an orange oil (1.8 g, 70%). Recrystallisation from acetone/dichloromethane gave an off-white solid (1.2 g, 47%). Tlc showed a trace of impurity, but $^1$H nmr, $^{13}$C nmr and IR showed the compound to be essentially pure 25-homodeoxycholic acid (4b)[2]: m.p. 169°-171° C. (softens at 167° C.) [Lit[2]. 160°-161° C.); $^1$H nmr (90MHz; CDCl$_3$/DMSO d$_6$) δ 0.65 (3H, s, 18-CH$_3$), 0.88 (3H, s, 19-CH$_3$), 2.1-2.3 (2H, t[broadened], 24-CH$_2$), 3.2-3.7 (1H, m, 3β-H), 3.8-4.0 (1H, m, 12β-H); $^{13}$C nmr (pyridine d$_5$/CD$_3$CN) δ 11.6 (C-18), 16.4 (C-21), 21.0 (C-23), 22.1 (C-19), 22.9 (C-15), 25.5 (C-16), 26.5 (C-7), 26.8 (C-6), 28.2 (C-11), 29.8 (C-2), 32.8 (C-9), 33.3 (C-10), 34.8, 35.2 (C-1, C-20, C-22, C-24), 35.8 (C-4), 36.2 (C-8), 41.4 (C-5), 45.7 (C-13), 46.2 (C-17), 47.2 (C-14), 70.0 (C-3), 71.4 (C-12), 174.9 (C-25); IR 3490, 3260 (OH's), 1702 (C=O) cm$^{-1}$.

The product was recrystallised again from acetone/dichloromethane before submitting for testing. Although tlc still showed some trace impurity on charring the plate, gas chromatography on the methyl ester (6b) [see below for details of prep.] showed the compound submitted for testing to be 97% pure. [procedure: The methyl ester (6b) (10 mg) was dissolved in pyridine (1.0 ml) and treated with hexamethydisilazane (0.2 ml) and trimethylchlorosilane (0.ml); 0.2μl of this solution was injected onto a BP-1 column 25 m×0.2 mm at 282° C.; chart speed 1.0 cm/min. Retention time 15.3 min; cf. retention time for methyl deoxycholate=12.6 min.].

9. Preparation of 25-homochenodeoxycholic acid (4c).

3α,7α-diformoxy-24-oxo-25-diazo-25-homocholane (3c) (2.0 g, 4.2 mmol) in collidine (5 ml) and benzyl alcohol (5 ml) was added to a preheated flask at 200° C. and heated with stirring at 180°-200° C. for 15 minutes. The reaction mixture was then cooled to ambient temperature, diluted with water (50 ml) and extracted into diethyl ether (4×). The combined ether extracts were then washed with water (1×), 2M HCl (2×), water (1×), sat. NaHCO$_3$ solution (1×), and water (3×), dried (MgSO$_4$) and evaporated. The resultant gum was then hydrolysed by dissolving in 10% methanolic KOH (40 ml) and refluxing for 1.5 hours. The resultant mixture was cooled to 0° C. and quenched with water (20 ml) and 2.5% K$_2$CO$_3$ solution (40 ml). The basic solution was then washed with ethyl acetate (3×) to remove the benzyl alcohol, acidified with 2M HCl and extracted into diethyl ether (3×). The combined ether extracts were washed with water (3×), dried (MgSO$_4$) and evaporated to afford a cream-coloured solid (1.2 g, 70%). Recrystallisation from acetone/dichloromethane gave a white solid (0.71 g, 41%). Tlc showed a trace of impurity, but $^1$H nmr, $^{13}$C nmr and IR showed the compound to be essentially pure 25-homochenodeoxycholic acid (4c)[3]: m.p. 217°-219° C. (softens at 210° C.) [Lit[3] 210°-212° C]; 1H nmr (90 MHz; CDCl$_3$/DMSO d$_6$) δ 0.64 (3H, s, 18-CH$_3$), 0.88 (3H, s, 19-CH$_3$), 2.1-2.3 (2H, m, 24-CH$_2$), 3.1-3.5 (1H, m, 3β-H), 3.6-3.8 (1H, m. 7β-H); $^{13}$C nmr (pyridine d$_5$/CD$_3$CN) δ 10.8 (C-18), 17.6 (C-21), 19.9 (C-11), 20.9 (C-23), 21.9 (C-19), 22.8 (C-15), 27.4 (C-16), 30.3 (C-2), 32.1 (C-9), 34.3 (C-6), 34.4 (C-10), 34.8, 34.9 (C-1, C-20, C-22, C-24), 38.9 (C-4), 39.4 (C-8, C-12), 41.3 (C-5), 41.6 (C-13), 49.7 (C-14), 55.2 (C-17), 66.6 (C-7), 70.5 (C-3), 175.0 (C-25); IR 3470, 3300 (OH's), 1698 (C=O) cm$^{-1}$.

The product was recrystallised again from acetome/dichloromethane before submitting for testing. Although tlc still showed some trace impurity on charring the plate, gas chromatography on the methyl ester (6c) [see below for details of prep.]showed the compound submitted for testing to be 96% pure. [GC procedure: The methyl ester (6c) (10 mg) was dissolved in pyridine (1.0 ml) and treated with hexamethyl disilazane (0.2 ml and trimethylchlorosilane (0.1 ml); 0.2 μl of this solution was injected onto a BP-1 column —25 m×0.2 mm at 282° C.; chart speed 1.0 cm/min. Retention time 15.7 min; cf. retention time for methyl chenodeoxycholate=13.2 min.].

PREPARATION OF THE METHYL ESTERS

10. Preparation of methyl chelate (5a).

Cholic acid (1a) (2.0 g, 4.9 mmol) in THF (40 ml) at 0° C. was treated dropwise with freshly prepared diazomethane in ether (prepared in the usual manner from diazald:diazald is N-methyl-N-nitroso-p-toluenesulphonamide) until the yellow colour persisted. After 15 minutes at 0° C. the solvent was evaporated to yield a white foam (2.1 g, 100%). Recrystallisation from methanol afforded pure methyl cholate (5a)[4] (1.3 g, 63%): m.p. 158°–159° C. (crystals began to melt 86°–88° C. and then resolidified—this was probably due to the retention of methanol in the crystals, see nmr data) [Lit[4] 156°–158° C.]; $^1$H nmr (60 MHz; CDCl$_3$) δ 0.66 (3H, s, 18-CH$_3$), 0.87 (3H, s, 19—CH$_3$), 3.0–3.6 (1H, m. 3β-H), 3.2–3.5 (3H, m [exchanges on adding D$_2$O], 3α,7α and 12α OH's), 3.48 (s, MeOH of crystallisation [ca. 1 mol equiv.]), 3.65 (3H, s, 24-OMe), 3.7–3.9 (1H, m, 7β-H), 3.8–4.0 (1H, m, 12β-H); IR (nujol mull) 3392, 3300 (OH's), 1734 (C=O) cm$^{-1}$.

The compound (5a) was submitted for testing without any further purification. Gas chromatography showed the product to be 96% pure [for GC procedure see prep. of (4a); retention time=13.6 min.].

11. Preparation of methyl deoxycholate (5b).

Deoxycholic acid (1b) (0.54 g, 1.4 mmol) in THF (10 ml) at 0° C. was treated dropwise with freshly prepared diazomethane in ether (prepared in the usual manner from diazald) until the yellow colour persisted. After 15 minutes at 0° C. the solvent was evaporated to yield a white foam (0.60 g). The compound would not recrystallise, although gas chromatography showed the product to be 99% pure [for GC procedure see prep. of (4b); retention time=12.6 min.]. The product was further purified by preparative silica tlc. (solvent system: EtOAc/CH$_2$Cl$_2$/AcOH—10:10:1) to afford pure methyl deoxycholate (5b)[5] (0.45 g, 80%) as a foam: [1]H nmr (60 MHz; CDCl$_3$) δ 0.67 (3H, s, 18-CH$_3$), 0.82 (3H, s, 19-CH$_3$), 2.18 (2H, s [exchanges on adding D$_2$O],3α and 12α OH's), 3.2–3.7 (1H, m. 3β-H), 3.65 (3H, s, 24-OMe), 3.8–4-1 (1H, m, 12β-H); IR (nujol mull) 3368 (OH's), 1740 (C=O) cm$^{-1}$; MS; Found m/z 288.2951 C$_{25}$H$_{40}$O$_3$(M-H$_2$O) requires m/z 388.2977.

The compound (5b) was submitted for testing without further purification.

12. Preparation of methyl chenodeoxycholate (5c)

Chenodeoxycholic acid (1c) (0.5 g, 1.3 mmol) in THF (10 ml) at 0° C. was treated dropwise with freshly prepared diazomethane in ether (prepared in the usual manner from diazald) until the yellow colour persisted. After 15 minutes at 0° C. the solvent was evaporated to yield a white foam (0.55 g). The compound would not recrystallise, although gas chromatography showed the product to be 97% pure [for GC procedure see prep. of (4c); retention time=13.2 min.]. The product was further purified by preparative silica tlc. (solvent system: EtOAc/CH$_2$Cl$_2$/AcOH—10:10:1) to afford pure methyl chenodeoxycholate (5c)[6] (0.42 g, 81%) as a foam: [1]H nmr (60 MHz; CDCl$_3$) δ 0.65 (3H, s, 18-CH$_3$), 0.80 (3H, s, 19-CH$_3$), 1.85 (2H, s [exchanges on adding D$_2$O], 3α and 7αOH's), 3.1-37 (1H, m, 3β-H), 3.64 (3H, s, 24-OMe), 3.7–3.9 (1H, m, 7β-H); IR (nujol mull) 3384 (OH's), 1740 (C=O) cm$^{-1}$; MS: Found m/z 406.3077; C$_{25}$H$_{42}$O$_4$(M) requires 406.3083.

The compound (5c) was submitted for testing without further purification.

13. Preparation of 25-homocholate (6a).

Homocholic acid (4a) (0.10 g, 0.24 mmol) in THF (6 ml) at 0° C. was treated dropwise with freshly prepared diazomethane in ether (prepared in the usual manner from diazald) until the yellow colour persisted. After 15 minutes at 20 C. the solvent was evaporated to yield a white foam (0.11g). Gas chromatography showed the product to be 99% pure [see prep. of (4a) for details]. Recrystallisation from acetone afforded pure methyl 25-homocholate (6a)[1] (46 mg. 45%): m.p. 155°–157° and 169°–170° C. [Lit[1a] 150°–151° and 166°–167° C.]; $^1$H nmr (60 MHz: CDCl$_3$) δ 0.67 (3H, s, 18-CH$_3$), 0.88 (3H, s, 19-CH$_3$), 3.0–3.6 (1H, m, 3β-H), 3.67 (3H, s, 24-OMe), 3.7–3.9 (1H, m, 7β-H), 3.8–4.1 (1H, m, 12β-H), IR (KBr) 3416 (OH's), 1738 (C=O) cm$^{-1}$.

The compound (6a) was submitted for testing without any further purification.

14. Preparation of methyl 25-homodeoxycholate (6b).

Homodeoxycholic acid (4b) (0.28 g, 0.69 mmol) in THF (8 ml) at 0° C. was treated dropwise with freshly prepared diazomethane in ether (prepared in the usual manner from diazald) until the yellow colour persisted. After 15 minutes at 0° C. the solvent was evaporated to yield a white foam (0.28 g, 97%). Gas chromatography showed the product to be 97% pure [see prep. of (4b) for details]. Recrystallisation from methanol afforded pure methyl 25-homodeoxycholate (6b)[2] (0.11 g, 38%): m.p. 126°–127° and 129°–131° C. [Lit[2] 125°–126° C.]; $^1$H nmr (60 MHz; CDCl$_3$) δ 0.67 (3H, s, 18-CH$_3$), 0.90 (3H, s, 19-CH $_3$), 3.3–3.7 (1H, m, 3β-H), 3.67 (3H, s, 24-OMe), 3.8–4.1 (1H, m, 12β-H); IR (KBr) 3412 (OH's), 1740 (C=O) cm$^{-1}$.

The compound (6b) was submitted for testing without any further purification.

15. Preparation of methyl 25-homochenodeoxycholate (6c)

Homochenodeoxycholic acid (4c) (0.19 g. 0.47 mmol) in THF (8 ml) at 0° C. was treated dropwise with freshly prepared diazomethane in ether (prepared in the usual manner from diazald) until the yellow colour persisted. After 15 minutes at 0° C. the solvent was evaporated to yield a white foam (0.20 g, 100%). Gas chromatography showed the product to be 96% pure [see prep. of (4c) for details). The product would not recrystallise. The product (0.12 g) was therefore combined with the product from a similar experiment (0.14 g) and further purified by preparative tlc. [solvent system: EtOAc/CH$_2$Cl$_2$/ACOH—10:10:11 to afford pure methyl 25-homochenodeoxycholate (6c)[3] (0.23 g, 89%): 1H nmr (60 MHz; CDCl$_3$) δ 0.66 (3H, s, 18-CH$_3$), 0.91 (3H, s, 19-CH$_3$), 1.82 (2H, s (exchanges on adding D$_2$O], 3β-OH and 7β-OH), 3.1–3.7 (1H, m, 3β-H), 3.68 (3H, s, 24-OMe), 3.7–4.0 (1H, m, 7β-H); IR (neat) 3392 (OH's), 1738 (C=O) cm$^{-1}$.

The compound (6c) was submitted for testing without any further purification.

PREPARATION OF THE BILE ALCOHOLS

Initially attempts were made to reduce cholic acid (1a) with LiAlH$_4$, but this reaction did not go to completion. Consequently, reduction of the methyl ester was found to be a better method of preparing the corresponding bile alcohol.

16. Preparation of 3α,7α,12α,24-tetrahydroxy-5β-cholane (7a)

A suspension of LiAlH$_4$ (0.06 g, 3 mols. equiv.) in dry THF (25 ml) was stirred under nitrogen whilst standing in an ice/methanol bath. Methyl cholate (5a) (0.22 g, 0.52 mmol) in dry THF (10 ml) was then added dropwise and the resultant mixture stirred at ambient temperature overnight. Water was then introduced carefully to the mixture until all the excess LiAlH₄ ad been destroyed. The resultant mixture was acidified with 2M HCl and extracted into EtOAc (3×). The combined organic extracts were washed with water (2×), dried and evaporated to give a white solid (0.17 g, 83%). Recrystallisation of 0.11 g from ethyl acetate afforded pure 3α,7α,12α,24-tetrahydroxy-5β-cholane (7a)[7] (40 mg., 31%): m.p. 226°–227° and 231°–234° C. [Lit.[7] 226°–227° C.]; $^1$H nmr (90 MHz; CDCl₃/DMSO d₆) δ 0.64 (3H, s, 18-CH₃), 0.85 (3H, s, 19-CH₃), 3.0–3.6 (4H, m [exchanges on adding D₂O], 3α-,7α-,12α- and 24-OH's), 3.0–3.6 (1H, m, 3β-H), 3.35–3.55 (2H, t[broadened], 24-CH₂), 3.6–3.8 (1H, m, 7β-H), 3.8–4.0 (1H, 12β-H); IR (KBr) 3382 (OH's) cm⁻¹.

The compound (7a) was submitted for testing without further purification.

17. Preparation of 3α,12α,24-trihydroxy-5β-cholane (7b).

A suspension of LiAlH₄ (0.15 g, 3 mols. equiv.) in dry THF (25 ml) was stirred under nitrogen whilst standing in an ice/methanol bath. Methyl deoxycholate (5b) (0.5 g, 1.2 mmol) in dry THF (30 ml) was then added dropwise and the resultant mixture stirred at ambient temperature for 2.5 hours. Water was then introduced carefully to the mixture until all the excess LiAlH₄ had been destroyed. The resultant mixture was acidified with 2M HCl and extracted into EtOAc (3×). The combined organic extracts were washed with water (2×), dried and evaporated to give a white foam (0.47 g, 100%). Recrystallisation of 0.41 g from ethyl acetate afforded pure 3α,12α,24-trihydroxy-5β-cholane (7b)[8] (0.30 g, 73%): m.p. 110°–116° C. [Lit[8] 107°–114° C.); $^1$H nmr (90 MHz; CDCl₃/DMSO d₆) δ 0.67 (3H, s, 18-CH₃), 0.90 (3H, s, 19-CH₃), 3.2–3.7 (1H, m, 3β-H), 3.4–3.6 (2H, t(broadened), 24-CH₂), 3.8–4.0 (1H, m, 12β-H); IR (KBr) 3366 (OH's) cm⁻¹.

The compound (7b) was submitted for testing without further purification.

18. Preparation of 3α,7α,24-trihydroxy-5β-cholane (7c).

A suspension of LiAlH₄ (0.15 g, 3 mols. equiv.) in dry THF (25 ml) was stirred under nitrogen whilst standing in an ice/methanol bath. Methyl chenodeoxycholate (5c) (0.5 g, 1.2 mmol) in dry THF (30 ml) was then added dropwise and the resultant mixture stirred at ambient temperature overnight. Water was then introduced carefully to the mixture until all the excess LiAlH₄ had been destroyed. The resultant mixture was acidified with 2M HCl and extracted into EtOAc (3×). The combined organic extracts were washed with water (2×), dried and evaporated to give a white foam (0.47 g. 100%). Recrystallisation of 0.27 g from dichloromethane afforded pure 3α,7α,24-trihydroxy-5β-cholane (7c)[3] (0.16 g, 59%): m.p. 116°–118° C. [Lit. [9a] 150° C.; also reported as an amorphous solid[9b]]; $^1$H nmr (90 MHz; CDCl₃/DMSO d₆) δ0.64 (3H, s, 18-CH₃), 0.88 (3H, s, 19-CH₃), 2.9–3.2 (2H, s (exchanges on adding D₂O], OH's, 3.1–3.6 (1H, m, 3β-H), 3.4–3.6 (2H, t[broadened], 24-CH₂), 3.6–4.0 (1H, m[exchanges on adding D₂O], OH), 3.7–3.9 (1H, m, 7β-H); IR (KBr) 3420 (OH's) cm⁻¹; MS: Found m/z 378.3130; C₂₄H₄₂O₃(M) requires m/z 378.3134.

The compound (7c) was submitted for testing without further purification.

19. Preparation of 3α,7α,12α,25-tetrahydroxy-25-homo-5β-cholane (7e).

A suspension of LiAlH₄ (0.15 g, 3 mols. equiv.) in dry THF (25 ml) was stirred under nitrogen whilst standing in an ice/methanol bath. Methyl homocholate (6a) (0.53 g, 1.2 mmol) in dry THF (50 ml) was then added dropwise and the resultant mixture stirred at ambient temperature overnight. Water was then introduced carefully to the mixture until all the excess LiAlH had been destroyed. The resultant mixture was acidified with 2M HCl and extracted into EtOAc (3×). The combined organic extracts were washed with water (2×), dried and evaporated to give a white solid (0.50 g, 100%). Recrystallisation from ethyl acetate afforded pure 3α,7α,12α,25-tetrahydroxy-25-homo-5β-cholane (7e) (0.26 g, 52%): m.p. 171°–172° and 192°–194° C.; $[\alpha]_D = +31.7°$ (c=1.0%; dioxane); $^1$H nmr (90 MHz; CDC₃/DMSO d₆) δ 0.64 (3H, s, 18-CH₃), 0.85 (3H, s, 19-CH₃), 3.1–3.6 (4H, m [exchanges on adding D₂O], 3α-,7α-,12α-, and 25-OH's), 3.2–3.6 (1H, m, 3β-H), 3.4–3.6 (2H, t[broadened], 24-CH₂), 3.6–3.8 (1H, m, 7β-H), 3.8–4.0 (1H, m, 12β-H); IR (KBr) 3384 (OH's) cm¹; MS : Found m/z 390.3129; C₂₅H₄₂O₃(M-H₂O) requires m/z 390.3134; *Elemental Analysis:* Found: C, 74.0; H, 11.0%; C₂₅H₄₄O₄ requires C, 73.5; H, 10.9%.

The compound (7e) was recrystallised again from ethyl acetate before submitting for testing.

20. Preparation of 3α,12α,25-trihydroxy-25-homo-5β-cholane (7b)

A suspension of LiAlH₄ (0.15 g, 3 mols. equiv.) in dry THF (25 ml) was stirred under nitrogen whilst standing in an ice/methanol bath. Methyl homodeoxycholate (6b) (0.54 g, 1.3 mmol) in dry THF (50 ml) was then added dropwise and the resultant mixture stirred at ambient temperature overnight. Water was then introduced carefully to the mixture until all the excess LiAlH had been destroyed. The resultant mixture was acidified with 2M HCl and extracted into EtOAc (3×). The combined organic extracts were washed with water (2×), dried and evaporated to give a white solid (0.50 g, 100%). Recrystallisation from ethyl acetate afforded pure 3α,12α,25-trihydroxy-25-homo-5β-cholane (7b) (0.26, 52%): m.p. 94°–97° C. $[\alpha]_D = +48.6°$ (c=1.0%; dioxane); (90 MHz; CDCl₃/DMSOd₆D₂O) δ 0.64 (3H, s, 18-CH₃), 0.88 (3H, s, 19-CH₃), 3.2–3.7 (1H, m, 3β-H), 3.4–3.6 (2H, t[broadened], 24-CH₂), 3.8–4.0 (1H, m, 12βt-H); IR (KBr) 3404 (OH's) cm⁻¹; MS Found m/z 374.3180; C₂₅H₄₂O₂(M-H₂O) requires m/z 374.3185; *Elemental Analysis:* Found: C, 75.5; H, 11.3%; C₂₅H₄₄O₃ requires C, 76.5; H, 11.3%.

The compound (7b) was recrystallised again from ethyl acetate before submitting for testing.

21. Preparation of 3α,7α,25-trihydroxy-25-homo-5β-cholane (7g).

A suspension of LiAlH₄ (0.15 g, 3 mols. equiv.) in dry THF (25 ml) was stirred under nitrogen whilst standing in an ice/methanol bath. Methyl homochenodeoxycholate (6c) (0.55 g, 1.3 mmol) in dry THF (50 ml) was then added dropwise and the resultant mixture stirred at ambient temperature overnight. Water was then introduced carefully to the mixture until all the excess LiAlH₄ had been destroyed. The resultant mixture was acidified with 2M HCl and extracted into EtOAc (3×). The combined organic extracts were washed with water (2×), dried and evaporated to give a white solid (0.51 g, 100%). Recrystallisation from ethyl acetate afforded pure 3α,7α,25-trihydroxy-25-homo-5β-cholane (7g) (0.23g, 45%): m.p. 185°-186.5° C.; $[\alpha]_D = +16.1°$ (c=0.9%; dioxane); $^1$H nmr (90 MHz; CDCl$_3$/DMSO d$_6$/D$_2$O) δ 0.65 (3H, s, 18-CH$_3$). 0.90 (3H, s, 19-CH$_3$), 3.2-3.7 (1H, m, 3β-H), 3.5-3.7 (2H, t[broadened], 24-CH$_2$), 3.7-3.9 (1H, m, 7β-H); IR (KBr) 3414 (OH's) cm$^{-1}$; MS: Found: m/z 392.3295; C$_{25}$H$_{44}$O$_3$(M) requires m/z 392.3290; *Elemental Analysis:* Found: C, 76.5; H, 11.4%; C$_{25}$H$_{44}$O$_3$ requires C, 76.5; H, 11.3%.

The compound (7g) was recrystallised again from ethyl acetate before submitting for testing.

REFERENCES

1a. W. H. Pearlman, J. Amer. Chem. Soc., 1947, 69, 1475.

b. B. Dayal, S. Shefer, G. S. Tint, G. Salen and E. H. Mosbach, J. lipid research, 1976, 17, 74.

2. H. Lettre, J. Greiner, K. Rutz, L. Hofmann, A. Egle and W. Bieger, Liebigs Ann. Chem., 1972, 758, 89.

3. B. I. Coben, G. S. Tint, T. Kuramoto and E. H. Mosbach, Steroids, 1975, 25, 365.

4. Elseviers Encyclopaedia of Org. Chem., 1962, 14, 3288s.

5. Elseviers Encyclopaedia of Org. Chem., 1962, 14, 3229s.

6. A. F. Hofmann, Acta Chem. Scand., 1963, 17, 173.

7. R. J. Bridgewater, T. Briggs, and G. A. D. Haslewood, Biochem. J., 1962, 82, 285.

8. R. T. Blickenstaff and F. C. Chang, J. Amer. Chem. Soc., 1959, 81, 2835.

9a. S. Ahmed, M. Alauddin, B. Caddy, M. Martin-Smith, W. T. L. Sidwell and T. R. Watson, Aust. J. Chem., 1971, 24, 521.

b. K. von Matumoto, J. Biochem. (Japan), 1955, 42, 207.

The following claims define some important aspects of the invention, but do not purport to include every conceivable aspect for which protection might be sought in subsequent continuing and foreign patent applications, and should not be construed as detracting from the generality of the inventive concepts hereinbefore described.

We claim:

1. A method of treatment of a fungal infection by a dermatophyte of the genus Trichophyton or Microsporum in a human patient in need of such treatment, which method comprises the step of administering topically to the patient a therapeutically effective amount of a compound of formula (7)

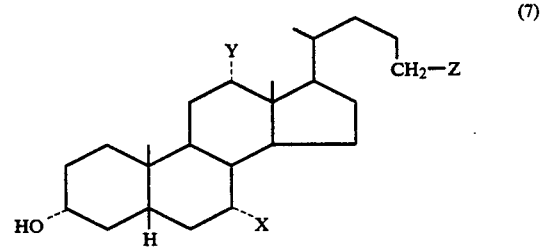

wherein X is a hydrogen atom or a hydroxyl group, Y is a hydrogen atom or a hydroxyl group and at least one of X and Y is a hydroxyl group and Z is a hydroxyl group or a methylol (—CH$_2$OH) group, provided that the compound wherein X and Y are hydroxyl and Z is methylol is used only for treatment of a fungal infection by a *Microsporum dermatophyte*.

2. The method according to claim 1, wherein ringworm is to be treated.

3. The method according to claim 1, wherein the compound of formula (7) is in which
   X is OH, Y is H, Z is OH; or
   X is H, Y is OH, Z is OH or —CH$_2$OH;
and athlete's foot is to be treated.

4. A method according to claim 1, wherein the compound of formula (7) is administered in an ointment or cream.

5. A method according to claim 4, wherein the ointment or cream contains from 1 to 5 weight percent of the compound of formula (7).

* * * * *